(12) United States Patent
Grass et al.

(10) Patent No.: US 8,431,638 B2
(45) Date of Patent: Apr. 30, 2013

(54) CITRIC ESTER MIXTURES AND THEIR USE

(75) Inventors: Michael Grass, Haltern am See (DE);
Stefan Buchholz, Hanau (DE); Wilfried Bueschken, Haltern am See (DE)

(73) Assignee: Evonik Oxeno GmbH, Marl (DE)

( * ) Notice: Subject to any disclaimer, the term of this patent is extended or adjusted under 35 U.S.C. 154(b) by 231 days.

(21) Appl. No.: 12/990,225

(22) PCT Filed: May 5, 2009

(86) PCT No.: PCT/EP2009/055410
§ 371 (c)(1),
(2), (4) Date: Oct. 29, 2010

(87) PCT Pub. No.: WO2009/146991
PCT Pub. Date: Dec. 10, 2009

(65) Prior Publication Data
US 2011/0046283 A1    Feb. 24, 2011

(30) Foreign Application Priority Data
Jun. 3, 2008 (DE) .......................... 10 2008 002 168

(51) Int. Cl.
*C08K 5/10* (2006.01)
(52) U.S. Cl.
USPC ........... 524/310; 524/284; 524/287; 524/317; 560/180
(58) Field of Classification Search .................. 524/285, 524/287, 310, 284, 301, 317; 560/180
See application file for complete search history.

(56) References Cited

U.S. PATENT DOCUMENTS

| | | |
|---|---|---|
| 6,534,577 B1 | 3/2003 | Keller |
| 7,595,421 B2 | 9/2009 | Grass et al. |
| 2002/0198402 A1 | 12/2002 | Bohnen et al. |

FOREIGN PATENT DOCUMENTS

| | | |
|---|---|---|
| EP | 1 063 257 | 12/2000 |
| EP | 1 256 566 | 11/2002 |
| EP | 1 864 964 | 12/2007 |
| JP | 53001521 | * 1/1978 |
| WO | 2007 038489 | 4/2007 |

OTHER PUBLICATIONS

Smolenskii, E.A., "Debranching Trees and Classification of Alkanes," Doklady Chemistry, vol. 379, No. 4-6, pp. 226-231, (Apr. 12, 2001).
Randic, M., "On Characterization of Molecular Branching," Journal of the American Chemical Society, vol. 97, No. 23, pp. 6609-6615, (Nov. 12, 1975).
International Search Report issued Dec. 2, 2009 in PCT/EP09/055410 filed May 5, 2009.

* cited by examiner

*Primary Examiner* — David W Wu
*Assistant Examiner* — Marie Reddick
(74) *Attorney, Agent, or Firm* — Oblon, Spivak, McClelland, Maier & Neustadt, L.L.P.

(57) ABSTRACT

The present invention relates to mixtures of citric esters of the formula I,

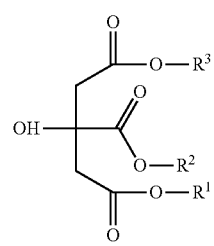

in which each of $R^1$, $R^2$ and $R^3$ is an aliphatic $C_5$ or $C_9$ moiety, wherein the average chain length of the aliphatic moieties in the mixture is in the range from greater than 5 to 7, and the average degree of branching of the aliphatic $C_9$ moieties is in the range from 0.9 to 2.2. The present invention also relates to the use of the citric ester mixture as a plasticizer in plastics compositions.

15 Claims, 1 Drawing Sheet

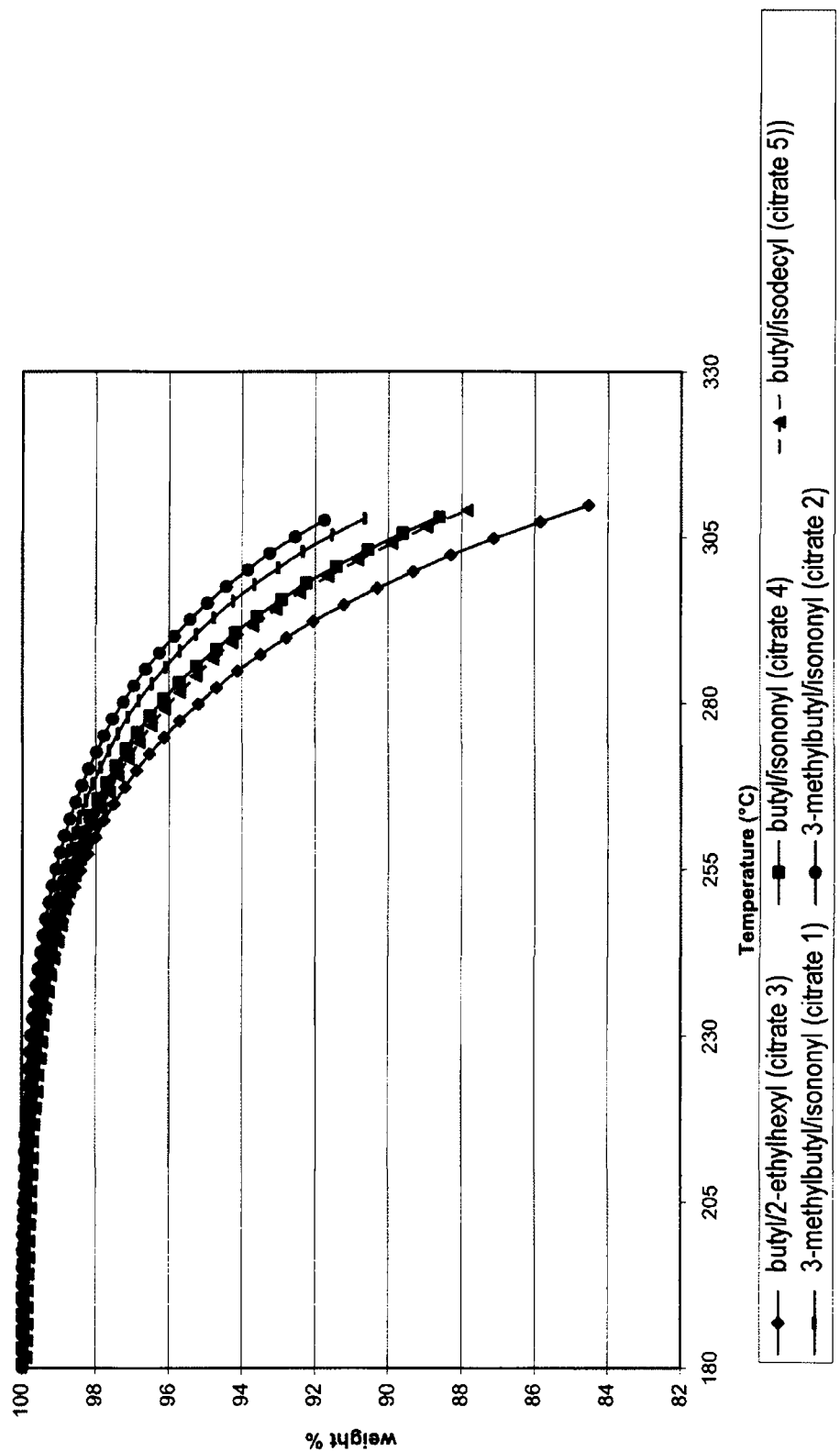

CITRIC ESTER MIXTURES AND THEIR USE

The present invention relates to mixtures composed of citric esters which comprise pentyl citrates, nonyl citrates and nonyl pentyl citrates, and also to their production and to their use as plasticizers for plastics.

Polyvinyl chloride (PVC) is one of the most important commercial polymers. It is widely used both in the form of unplasticized PVC and in the form of plasticized PVC.

To produce plasticized PVC, plasticizers are added to the PVC, those used in most cases being phthalic esters, in particular di-2-ethylhexyl phthalate (DEHP), diisononyl phthalate (DINP) and diisodecyl phthalate (DIDP).

Discussions about reproduction-toxicity effects have in some cases already led to an increased level of identification marking under hazardous-materials legislation, and have also led to limitations on use in toys for toddlers, and it therefore has to be assumed that the use of these phthalates will reduce markedly in the future, particularly in sensitive applications, such as food packaging and medical applications. Various environmental organizations are also demanding general replacement of phthalates specifically in applications for interiors, e.g. in floor coverings, wallpapers and synthetic leathers.

There is therefore a need for plasticizers which are not subject to identification-marking requirements and which can be used as replacement for DEHP or for DINP, and which are produced from raw materials of which large quantities are available worldwide.

One conceivable alternative is the use of plasticizers based on citric acid, especially because this acid is obtainable from renewable raw materials. It is known that citric esters with three identical alkyl moieties can be used, examples being tri-n-butyl citrate or tri-2-ethylhexyl citrate (e.g. Gächter/Müller, Kunststoffadditive [Plastics additives], 3rd edition 1990, Carl Hanser-Verlag, pages 417-418). DE 10 2006 026 624 describes citric esters based on primary $C_5$ alcohols. These esters are then often derivatized by acetylating the free hydroxy group of the citric triester with a carboxylic acid or with a carboxylic acid derivative, for example with the anhydride. The best-known citric-acid-based plasticizer has hitherto been tri-n-butyl acetylcitrate (TBAC), which is a substance also having various approvals for sensitive applications.

Corresponding acylation processes are disclosed by way of example in DE 1 099 523. DE 35 20 750 also discloses citric ester mixtures of this type or mixtures of acetyl derivatives thereof having various alkyl moieties, an example being an ester mixture having n-hexyl, n-octyl and n-decyl moieties.

Citric esters, or mixtures of citric esters, which are used as plasticizers are intended to comply with a number of requirements: their volatility has to be low, so that processing results in only small plasticizer losses and little pollution of the environment. By way of example, TBAC is not ideal in this respect. The compatibility of the plasticizers with the plastic to be plasticized must be sufficiently large to permit incorporation of a large amount thereof into the plastic and to prevent significant exudation of the plasticizer from the plastic even on prolonged use. The materials have to bring about good processing properties in mixtures with the plastic. A particularly important factor is adequate suitability for the major application sector of plastisol processing. If a citric ester is to be used to replace a particular plasticizer (for example DINP), maximum similarity of properties would be desirable, since this minimizes the cost of reformulation and resetting of process parameters. The most important properties here would be plastisol viscosity, gelling and efficiency (amount of plasticizer needed to achieve a certain degree of softness).

A further intention is that the citric esters or their mixtures be capable of production from materials which are readily available and inexpensive.

EP 1 256 566 describes a plasticizer composed of a mixture of tri-n-butyl citrate, di-n-butyl 2-ethylhexyl citrate, n-butyl di-2-ethylhexyl citrate and tri-2-ethylhexyl citrate. This plasticizer features low volatility and good compatibility with PVC. There are no other positive features disclosed.

WO 2007/038489 likewise discloses, as plasticizers, citrate mixtures having two different alkyl moieties, which differ by at least 4 carbon atoms. These citrate mixtures are intended to have relatively low volatility and to bring about good performance characteristics in the plasticized PVC. In the example, a citrate mixture is produced via esterification of citric acid with n-butanol and isononanol, and is then acetylated. The mixture involved is therefore composed of tri-n-butyl acetylcitrate, di-n-butyl isononyl acetylcitrate, n-butyl di-isononyl acetylcitrate and tri-isononyl acetylcitrate.

EP 1 063257 B1 claims citric ester mixtures as plasticizers for PVC, where the alcohol component of these encompasses a mixture of various alcohols having a chain length range of $C_5$ to $C_{12}$. The document does not reveal whether the citric acid is esterified with two or more alcohols, or whether the alcohols have the same or a different number of carbon atoms, or whether the materials involve primary, secondary or tertiary alcohols or a mixture thereof. In example 1, a citric ester mixture is produced by reacting citric acid with alcohols having a chain length range of from $C_6$ to $C_{10}$. This statement is ambiguous. "Alcohols having a chain length of from $C_6$ to $C_{10}$" can mean that alcohols are present respectively having 6, 7, 8, 9 and 10 carbon atoms, but can also mean two or more isomeric alcohols or two or more alcohols with different carbon number or isomeric alcohols together with alcohols of another carbon number. The molar ratio of the alcohols to one another, and the nature of the alcohols (primary, secondary, tertiary) is moreover not stated. In other words, an infinite number of citrate ester mixtures with different properties is possible. There is no property profile allocated to any defined citrate ester mixture.

Since the known citric esters and their mixtures do not correspond in every respect to the desired requirements profile, the object was to deliver a plasticizer with improved properties, based on citric acid.

The said plasticizer should be capable of replacing DINP, which hitherto has been a standard plasticizer, at minimum cost. The plasticizer should moreover comprise no components which are defined by the AGBB (German committee for evaluating health effects of construction products, found by way of example at http://www.umweltbundesamt.de/bau-produkte/agbb.htm) as SVOC components (low-volatility organic compounds) with retention range from $C_{16}$ to $C_{22}$ on a nonpolar gas chromatography column (see Example 7).

Regulations concerning the approval of construction products in occupied areas of buildings were tightened a few years ago. A factor common to practically all national standards is the definition of a maximum value for VOC emitted after a certain period of storage in an emission test chamber. In addition, applicable only in Germany, there are strict threshold values for low-volatility compounds (SVOCs).

Processors have more freedom of formulation when these compounds are not present. These esters according to the invention can therefore be used for the production of items for interior use. The volatility of the citric ester mixtures according to the invention is moreover lower than that of butyl/2-ethylhexyl, butyl/isononyl and butyl/isodecyl citrates with the same average chain length of the alkyl groups (see Example 6). The intention was that the hydroxy group be non-acylated, particularly for reasons of cost.

Surprisingly, it has been found that mixtures of citric esters whose hydroxy group has not been acetylated and whose alkyl moieties bonded at the oxygen of the carboxy group are exclusively $C_5$ or $C_9$ moieties, and whose average chain length is in the range from greater than 5 to 7, where the average degree of branching of the aliphatic $C_9$ moieties is in the range from 0.9 to 2.2, satisfy the desired requirements.

BRIEF DESCRIPTION OF THE DRAWING

FIG. 1 illustrates a comparison of test curves wherein the losses in weight of citrates 1 through 5 produced according to Example 1 are compared at relatively high temperatures by the dynamic TGA method.

The present inventions provide mixtures of citric esters of the formula I,

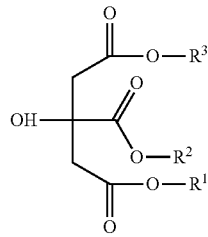

I in which each of $R^1$, $R^2$ and $R^3$ is an aliphatic $C_5$ or $C_9$ moiety, characterized in that the average chain length of the aliphatic moieties in the mixture is in the range from greater than 5 to 7, and the average degree of branching of the aliphatic $C_9$ moieties is in the range from 0.9 to 2.2.

These mixtures of citric esters include the respective mixed citric esters based on the aliphatic $C_5$ and $C_9$ alcohols used, e.g. a dinonyl pentyl citrate.

The present invention also provides the use of the citric ester mixture according to the invention as plasticizers in plastics compositions.

The present invention also provides a composition comprising the citric ester mixture according to the invention in a mixture with further components, comprising plasticizers from the group of the alkyl esters of the aromatic polycarboxylic acids, of the cyclohexanepolycarboxylic acids, of benzoic acid or of adipic acid, and also the use of this type of plasticizer composition in plastics compositions, in adhesives, in sealing compounds, in coatings, in paints, in plastisols or in inks. Plastics products produced from the plasticizers according to the invention can by way of example be profiles, gaskets, food packaging, foils, toys, medical items, roof sheeting, synthetic leather, floor coverings, underbody protection, coated textiles, wallpapers, cables and wire sheathing.

The ester mixtures according to the invention have high compatibilities with plastics and have good performance characteristics. In one particular embodiment, the citric ester mixtures according to the invention are capable of replacing DINP, which is currently the most important plasticizer in Europe, without major formulation changes, since the most important properties:
 plastisol viscosities,
 gelling and
 plasticizing effect
are almost identical (see Examples 3, 4 and 5). The rise in viscosities with time (aging) is moreover markedly smaller than with other citrates.

For characterization of the citric ester mixture of the general formula I

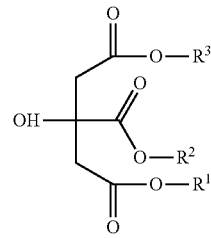

I the average chain length or the average number of carbon atoms of the aliphatic $C_5$ or $C_9$ moieties $R^1$, $R^2$ and $R^3$ bonded at the oxygen of the carboxylate groups is used. In the present invention, the average number of the carbon atoms $C_d$ of the alkyl moieties $R^1$, $R^2$ and $R^3$ bonded at the oxygen of the carboxylate group is in the range from greater than 5 to 7, in particular in the range from 5.5 to 6.8.

In the case of a mixed citric ester composed of two alcohols using a mols of an alcohol having x carbon atoms and b mols of an alcohol having y carbon atoms, the average chain length is calculated as average number of carbon atoms $C_d$ of the alkyl side chain as follows:

$$C_d = (a*x + b*y)/(a+b)$$

If $n_1$ is the molar amount of the $C_5$ moieties in a certain amount of the citric ester and $n_2$ is the corresponding molar amount of $C_9$ moieties in the same amount, the average number of carbon atoms $C_d$ is calculated as follows:

$$C_d = (5n_1 + 9n_2)/(n_1 + n_2)$$

Using $v = n_1/n_2$ for the ratio of the molar amounts of $C_5$ moieties and $C_9$ moieties, the following applies for the average chain length of the alkyl moieties, or $C_d$:

$$C_d = (5v + 9)/(v + 1)$$

If, by way of example, the amounts of $C_5$ moieties and $C_9$ moieties are equimolar, the average chain length of the alkyl moieties, or the value of $C_d$, is calculated as 7.

According to the invention, the $C_5$ moieties can have the following structures:
n-pentyl ($-CH_2-CH_2-CH_2-CH_2-CH_3$)
2-methylbutyl ($-CH_2-CH(CH_3)-CH_2-CH_3$)
3-methylbutyl ($-CH_2-CH_2-CH(CH_3)-CH_3$)
2,2-dimethylpropyl ($-CH_2-C(CH_3)_2-CH_3$)

It is preferable that the citric ester mixtures according to the invention comprise n-pentyl and/or 3-methylbutyl moieties. In particular, the proportion of the entirety of n-pentyl and 3-methylbutyl moieties, based on the entirety of the pentyl moieties, is greater than 90%, very particularly preferably greater than 95%. The proportion of 2,2-dimethylpropyl moieties is preferably below 2%, very particularly preferably below 1%. It is particularly preferable that the content of 3-methylbutanol, based on the entirety of the pentyl moieties, is greater than 70%, in particular greater than 80%, very particularly preferably greater than 90%.

The $C_9$ moieties ($-CH_2-C_8H_{17}$) in the ester mixture according to the invention can likewise have various structures, and the $-C_8H_{17}$ group of the $C_9$ moiety here can be linear, singly branched, doubly branched or multi-branched. It is preferable that the ester mixture comprises a large number of isomeric $C_9$ moieties whose average degree of branching can preferably be from 0.9 to 2.2 and particularly preferably from 1.0 to 2.0.

$^1$H or $^{13}$C NMR spectroscopy methods can be used to determine the average degree of branching of the $C_9$ moieties in the citric ester mixtures.

The following methods can be used to produce the citric ester mixtures I according to the invention:
  a) esterification of citric acid, citric acid monohydrate or citric anhydride with pentanols and nonanols
  b) transesterification of citric esters, such as trimethyl citrate or triethyl citrate, with pentanols and nonanols
  c) transesterification of a pentyl citrate or corresponding mixture with a nonyl citrate or corresponding mixture
  d) mixing of the respective mixed citric esters based on the aliphatic $C_5$ and $C_9$ alcohols used
  e) mixing of trinonyl citrates with tripentyl citrates It is preferable that the mixture according to the invention is produced by method a).

Another preferred production method is the combination of methods a) and b). The citric acid here or one of its anhydrides is esterified with pentanol or with a pentanol mixture to give pentyl ester(s), and excess pentanol serves here as entrainer for water. The resultant tripentyl ester is then transesterified with the calculated amount of nonanol. Distillation can optionally be used to modify the constitution of the citric ester mixtures.

In the case of the esterification of citric acid or of a citric acid hydrate with the corresponding alcohol or alcohol mixture, the alcohol component is used in stoichiometric excess. The alcohol component is reactant and entrainer for removal of the water of reaction, and, if appropriate, of the water introduced with the citric acid. The stoichiometric excess is preferably from 5 to 50%, in particular from 10 to 40%, particularly preferably from 15 to 35%.

The esterification is preferably carried out in the presence of an esterification catalyst. Catalysts that can be used are in principle acids, such as sulphuric acid, methanesulphonic acid or p-toluenesulphonic acid, or other mineral acids, or metals or compounds of these. Examples of those suitable are tin, titanium, and zirconium, where these can be used in the form of finely divided metals or advantageously in the form of their salts or oxides, or in the form of soluble organic compounds. However, the metal catalysts are unlike the proton acids in being high-temperature catalysts whose full activity is often not reached until temperatures above 180° C. have been attained.

The catalyst concentration can be varied within a wide range, as a function of the nature of the catalyst. For proton acids, concentrations of from 0.05 to 2% by weight are usual, preferably from 0.1 to 1% by weight, particularly preferably from 0.15 to 0.5% by weight. Although higher acid concentrations increase the reaction rate, they can favour side-reactions. By way of example, in order to avoid elimination of water from citric acid or its partial or full esters it is advantageous to carry out the esterification in the temperature range from 120° C. to 180° C., preferably from 130° C. to 170° C., and very particularly preferably from 155° C. to 165° C.

The aliphatic $C_9$ alcohols to be used are commercially available on the market with various constitutions. For the purposes of this invention, it is also possible to use nonanol mixtures which comprise not only $C_9$ alcohols but also amounts of $C_8$ alcohols, and also of $C_{10}$ alcohols.

The $C_9$ alcohol component used in the esterification preferably comprises a $C_9$ alcohol mixture obtained via hydroformylation of a $C_8$ olefin mixture produced via oligomerization of linear butenes by the Octol process on a nickel-containing catalyst, and subsequent hydrogenation.

The citric ester mixtures according to the invention can be used as plasticizers, in particular in plastics compositions, in adhesives, in sealing compounds, in coatings, in paints, in plastisols, in synthetic leathers, in floor coverings, in underbody protection, in coated textiles, in wallpapers or in inks. It is preferable that the plasticizers according to the invention can be used in profiles, gaskets, food packaging, foils, toys, medical items, roof sheeting, synthetic leathers, floor coverings, underbody protection, coated textiles, wallpapers, cables and wire sheathing, and it is particularly preferable that they can be used in food packaging, toys, medical items, wallpapers and floor coverings.

Using the citric ester mixtures according to the invention it is in particular possible to obtain compositions according to the invention which comprise the citric ester mixture.

These compositions can comprise the citric ester mixture according to the invention alone or in a mixture with other plasticizers. If the compositions according to the invention comprise the citric ester mixture according to the invention in a mixture with other plasticizers, the other plasticizers can preferably have been selected from the group of the dialkyl phthalates, preferably having from 4 to 13 carbon atoms in the alkyl chain; trialkyl trimellitates, preferably having from 4 to 10 carbon atoms in the side chain; dialkyl adipates, and preferably dialkyl terephthalates, in each case preferably having from 4 to 10 carbon atoms in the side chain; alkyl 1,2-cyclohexanedicarboxylates, alkyl 1,3-cyclohexanedicarboxylates and alkyl 1,4-cyclohexanedicarboxylates, preferably alkyl 1,2-cyclohexanedicarboxylates, in each case preferably having alkyl=alkyl moiety having from 4 to 10 carbon atoms in the side chain; dibenzoic esters of glycols, preferably with di- or triethylene glycol, or else di- or tripropylene glycol; alkylsulphonic esters of phenol preferably having an alkyl moiety which comprises from 8 to 22 carbon atoms; polymeric plasticizers, glycerol esters and alkyl benzoates, preferably having from 7 to 13 carbon atoms in the alkyl chain. In all cases, the alkyl moieties can be linear or branched, and also identical or different. It is particularly preferable that the composition comprises, alongside citric ester mixtures, in particular an alkyl benzoate having alkyl=alkyl moiety having from 7 to 13 carbon atoms, preferably isononyl benzoate, nonyl benzoate, isodecyl benzoate, propylheptyl benzoate, or decyl benzoate. The proportion of citric ester mixtures according to the invention in the mixture with other plasticizers is preferably from 15 to 90%, particularly preferably from 20 to 80% and very particularly preferably from 30 to 70%, where the proportions by weight of all of the plasticizers present give a total of 100%.

The compositions mentioned, composed of citric ester mixtures and of other plasticizers, can be used as plasticizer composition in plastics compositions, or in adhesives, in sealing compounds, in coatings, in paints, in plastisols or in inks. Plastics products produced from the plasticizer compositions according to the invention can by way of example be: profiles, gaskets, food packaging, foils, toys, medical items, roof sheeting, synthetic leather, floor coverings, underbody protection, coated textiles, wallpapers, cables and wire sheathing. From this group, preference is given to food packaging, toys, medical items, wallpapers, coated textiles, synthetic leather and floor coverings.

The compositions according to the invention which comprise a citric ester mixture can comprise a polymer selected from polyvinylchloride (PVC), polyvinylidene chloride (PVDC), polyacrylates, in particular polymethyl methacrylate (PMMA), polyalkyl methacrylate (PAMA), fluoropolymers, in particular polyvinylidene fluoride (PVDF), polytetrafluoroethylene (PTFE), polyvinyl acetate (PVAc), polyvinyl alcohol (PVA), polyvinyl acetals, in particular polyvinyl butyral (PVB), polystyrenepolymers, in particular polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid-copolymer, polyolefins, in particular polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, in particular polylactic acid (PLA), polyhydroxybutyric acid (PHB), polyhydroxyvaleric acid (PHV), polyester, starch, cellulose and cellulose derivatives, in particular nitrocellulose (NC), ethylcellulose (EC), cellulose acetate (CA), cellulose acetate/butyrate (CAB), rubber or silicones, and also mixtures or copolymers of the polymers mentioned or of their monomeric units. The inventive compositions preferably comprise PVC or homo- or copolymers based on ethylene, on propylene, on butadiene, on vinyl acetate, on glycidyl acrylate, on glycidyl methacrylate, on methacrylates, on acrylates, or on acrylates or methacrylates having, bonded to the oxygen atom of the ester group, alkyl moieties of branched or unbranched alcohols having from one to ten carbon atoms, or on styrene, on acrylonitrile, or on cyclic olefins.

The composition according to the invention in the form of a grade of PVC preferably comprises suspension PVC, bulk PVC, microsuspension PVC or emulsion PVC. Based on 100 parts by weight of polymer, the compositions according to the invention preferably comprise from 5 to 200, with preference from 10 to 150, parts by weight of plasticizer.

The compositions according to the invention can comprise, alongside the constituents mentioned, other constituents, particular examples being other plasticizers, fillers, pigments, stabilizers, costabilizers, such as epoxidized soya bean oil, lubricants, blowing agents, kickers, antioxidants or biocides.

The compositions comprising polymers mentioned can be used in the form of plastics compositions, adhesives, sealing compounds, coatings, paints, plastisols, synthetic leather, floor coverings, underbody protection, textile coatings, wallpapers or inks, or for the production of these. The compositions mentioned can in particular be profiles, gaskets, food packaging, foils, toys, medical items, roof sheeting, synthetic leather, floor coverings, underbody protection, coated textiles, wallpapers, cables and wire sheathing. The compositions are preferably food packaging, toys, medical items, wallpapers and floor coverings.

The examples below are intended to illustrate the invention but not to restrict the invention thereto.

EXAMPLES

Example 1

Synthesis of the Citric Esters

In each case, citric acid monohydrate was esterified according to the following specification with the mixtures listed in Table 1 of a relatively short-chain alcohol (A1) and of a relatively long-chain alcohol (A2). The alcohol mixtures were produced in advance and in each case represent an excess of 33%, based on the citric acid.

1050 g of citric acid monohydrate (5 mol) and initially 800 g of alcohol mixture according to Table 1 were used as initial charge in a 4 liter distillation flask. The contents of the flask and the esterification apparatus were first flushed with nitrogen for 30 minutes by way of a dip tube. The stirrer was switched on at a low rotation rate, and the mixture was slowly heated. Starting at about 115° C., water of crystallization separated from the acid, and was removed by way of a water separator. At 145° C., 3.15 g of sulphuric acid (0.3% by weight, based on the carboxylic acid) diluted in 50 ml of alcohol mixture was added dropwise by way of an attached dropping funnel, which was flushed with nitrogen for about 5 minutes prior to the addition. The dropping funnel was maintained under nitrogen during the addition.

Once the reaction temperature of 160° C. had been achieved, the remaining amount of alcohol was slowly added. Care was taken here to keep the temperature constant. The water of reaction produced was regularly removed. Once all of the alcohol had been added, reflux was maintained at constant temperature by adding toluene. After from 5 to 7 hours, the reaction was terminated, since the acid number had fallen below 1 mg KOH/g. The mixture was then cooled, while the flow of nitrogen was continued. The reaction product was then transferred to a 4 L reaction flask equipped with blade stirrer, dip tube with superposed dropping funnel and thermometer, on a Claisen bridge. Here again, care was taken to maintain the inert gas atmosphere. Nitrogen flushing was continued for a further 15 minutes, and then a vacuum was applied, and the heating was switched on after 15 minutes. The added toluene and the excess of alcohol were removed by distillation under maximum vacuum at up to 160° C., and then the acid number of the residue was determined to DIN EN ISO 2114, and the residue was neutralized with ten times the stoichiometric amount of sodium hydroxide solution (5% by weight in water). For this, the hydroxide solution was slowly added dropwise at 80° C. under atmospheric pressure by way of the dropping funnel. Once addition was complete, the mixture was stirred at 80° C. for 30 minutes. The stirrer was then switched off. The aqueous phase was discharged after a settling time of 30 minutes.

5% aqueous sodium chloride solution was then added (25% by weight, based on the reactor contents) to the crude ester, and the mixture was stirred at 80° C. for 15 minutes. The stirrer was then switched off. The aqueous phase was discharged after a settling time of 30 minutes.

2% of activated charcoal (CAP Super, Norit), based on the reactor contents, were then added to the neutralized ester and the reactor was evacuated and heated to 140° C. Nitrogen was passed into the product by way of a dip tube. The vacuum was set to 40 mbar by way of the nitrogen stream, and the product was stripped for 30 minutes.

The apparatus was then cooled to 80° C.

The product was filtered by way of a suction flask with suction funnel containing a filter paper on which a filter cake composed of filtration aid had previously been compacted.

The purity of the resultant esters was then determined by gas chromatography. In all cases it was above 99.7%.

TABLE 1

| Example | A1 | Amount of A1 in g (mol) | A2 | Amount of A2 in g (mol) | Average carbon number $C_d$ |
|---|---|---|---|---|---|
| 1 (according to the invention) | 3-methylbutanol (Aldrich) | 1408 (16) | isononanol (Evonik Oxeno) | 576 (4) | 5.8 |
| 2 (according to the invention) | 3-methylbutanol (Aldrich) | 1179 (13.4) | isononanol (Evonik Oxeno) | 950 (6.6) | 6.3 |

TABLE 1-continued

| Example | A1 | Amount of A1 in g (mol) | A2 | Amount of A2 in g (mol) | Average carbon number $C_d$ |
|---|---|---|---|---|---|
| 3 | n-butanol (OXEA) | 814 (11) | 2-ethylhexanol (OXEA) | 1170 (9) | 5.8 |
| 4 | n-butanol (OXEA) | 947 (12.8) | isononanol (Evonik Oxeno) | 1037 (7.2) | 5.8 |
| 5 | n-butanol (OXEA) | 1036 (14) | isodecanol (Exxal 10 from ExxonMobil) | 924 (6) | 5.8 |

Example 2

Production of Plastisols

The starting weights used of the components for the various plastisols can be found in Table 2 below.

TABLE 2

Formulations [all data in phr (=parts by weight per 100 parts by weight of PVC)]

| Plastisol formulation | 1 | 2 | 3 | 4 | 5 | 6 |
|---|---|---|---|---|---|---|
| Vestolit B 7021 (Vestolit GmbH) | 100 | 100 | 100 | 100 | 100 | 100 |
| Vestinol 9 (DINP from Evonik Oxeno GmbH) | 50 | | | | | |
| Citrate 1 (according to the invention) | | 50 | | | | |
| Citrate 2 (according to the invention) | | | 50 | | | |
| Citrate 3 (comparative example) | | | | 50 | | |
| Citrate 4 (comparative example) | | | | | 50 | |
| Citrate 5 (comparative example) | | | | | | 50 |
| Epoxidized soya bean oil (Drapex 39, Chemtura) | 3 | 3 | 3 | 3 | 3 | 3 |
| OBS 1100, stabilizer (Chemtura) | 0.6 | 0.6 | 0.6 | 0.6 | 0.6 | 0.6 |
| Mark CH 302, co-stabilizer (Chemtura) | 1.8 | 1.8 | 1.8 | 1.8 | 1.8 | 1.8 |

The temperature of the plasticizers was controlled to 25° C., prior to addition. The liquid constituents were first weighed into a PE beaker and were followed by the pulverulent constituents. The mixture was mixed manually with a paste spatula until all the powder had been wetted. The mixing beaker was then clamped into the clamping equipment of a dissolver mixer. Prior to immersing the stirrer into the mixture, the rotation rate was set to 1800 revolutions per minute. Once the stirrer had been switched on, stirring was continued until the temperature on the digital display of the temperature sensor reached 30.0° C. This ensured that the plastisol was homogenized with defined energy input. The temperature of the plastisol was then immediately brought to 25° C.

Example 3

Measurement of Plastisol Viscosity

The viscosities of the plastisols produced in Example 2 were measured as follows using a Physica DSR 4000 rheometer (Paar-Physica) controlled by the associated US 200 software.

The plastisol was again stirred with a spatula in the storage vessel, and was tested in test system Z3 (DIN 25 mm) in accordance with the operating instructions. The measurement was made automatically at 25° C. by way of the abovementioned software. The settings were as follows:

Pre-shear of 100 s$^{-1}$ for a period of 60 s, during which no values were measured.

A downward progression beginning at 200 s$^{-1}$ and ending at 0.1 s$^{-1}$, divided into a logarithmic series with 30 steps, the duration for each point of measurement being 5 s.

After the test, the test data were processed automatically by the software. The viscosity was plotted as a function of shear rate. The measurements were made respectively after 2 h, 24 h and 7 days. The paste was stored at 25° C. between these junctures.

The corresponding viscosity values obtained after the respective storage times stated are listed by way of example in Table 3 below for a shear rate of 100 s$^{-1}$.

TABLE 3

Plastisol viscosities at shear rate of 100 s$^{-1}$

| Plastisol No. | Viscosity after 2 hours in Pa · s | Viscosity after 24 hours in Pa · s | Viscosity after 7 days in Pa · s | % Rise |
|---|---|---|---|---|
| 1 | 6.88 | 7.15 | 7.19 | 4.5 |
| 2 | 6.20 | 6.78 | 7.0 | 13 |
| 3 | 6.67 | 7.44 | 7.19 | 7.8 |
| 4 | 5.43 | 6.17 | 6.83 | 25.7 |
| 5 | 5.32 | 5.97 | 6.57 | 23.5 |
| 6 | 5.96 | 6.71 | 7.22 | 21.1 |

Summary: The viscosities of the plastisols derived from the two citric ester mixtures of the invention are practically the same as that of the mixture using DINP. The overall level of the three comparative citrate plastisols (plastisols 4-6) is somewhat lower, and they moreover exhibit a markedly higher increase in viscosity over time. The latter, in particular, implies higher operating costs for processors. This is another reason for preferring the plastisols according to the invention.

Example 4

Measurement of Gelling Rate

The gelling behaviour of the plastisols was studied in a Bohlin CVO oscillation viscometer (PP20 measurement system) operated with shear stress control.

The parameters set were as follows:

Mode:
   temperature gradient
   starting temperature: 25° C.
   final temperature: 180° C.
   heating/cooling rate: 2° C./min
   temperature after measurement: 25° C.
   oscillation frequency: 2 Hz
   delay time: 1 s
   waiting time: 15 s
   continuous oscillation: on
   automatic shear stress preset: on
   starting shear stress: 0.3 Pa
   setpoint deformation: 0.002
   gap width: 0.5 mm Measurement Method:

A spatula was used to apply a drop of the plastisol formulation to be tested, free from air bubbles, to the lower plate of the test system. Care was taken here to ensure that some plastisol could exude uniformly out of the test system (not more than about 6 mm overall) after the test system had been closed. The protective covering, which also serves for thermal insulation, is then superposed, and the test is started.

The "complex viscosity" of the plastisol was determined as a function of temperature. The start of gelling was recognizable via a sudden marked rise in complex viscosity. The earlier the onset of this viscosity rise, the better the gelling capability of the system. For comparison purposes, an interpolation method was used on the curves for each plastisol to determine the temperature at which a complex viscosity of 1000 Pa*s had been reached.

The values obtained here are listed in Table 4:

TABLE 4

Gelling behaviour

| | Plastisol number according to Example 2 | | | | | |
|---|---|---|---|---|---|---|
| | 1 | 2 | 3 | 4 | 5 | 6 |
| Temperature for viscosity of 1000 Pa * s | 92° C. | 91° C. | 94° C. | 85° C. | 86° C. | 88° C. |

The two citric ester mixtures according to the invention (in plastisols 2 and 3) in their respective formulations exhibit gelling behaviour very similar to that of DINP.

Example 5

Measurement of Shore Hardness of Cast Specimens

Shore A hardness is a measure of the softness of a test specimen. The greater the penetration of a standardized needle into the test specimen during a certain test time, the lower the value measured. The plasticizer with the highest efficiency gives the lowest value for Shore hardness for the same amount of plasticizer. Conversely, in the case of highly efficient plasticizers it is possible to make a certain reduction in the proportion in the formulation, and in many instances this is reduces processors' costs.

To determine Shore hardness values, the plastisols produced according to Example 2 were cast in circular casting moulds of diameter 50 mm. Plastisols were then gelled at 200° C. for 10 min in the moulds in a convection oven, and removed after cooling, and, prior to measurement, stored for at least 16 hours under standardized conditions of temperature and humidity (23° C.; 50% relative humidity). The thickness of the discs was about 8 mm.

The actual tests were carried out to DIN 53 505, using Shore A test equipment from Zwick-Roell, and in each case the measured value was read after 3 seconds. Three different measurements were carried out at various points on each test specimen (not in the edge region), and in each case the average value was noted.

Table 5 lists the measured values obtained.

TABLE 5

Shore hardness values

| Plastisol number (see Table 2) | Alcohol mixture | Shore hardness |
|---|---|---|
| 1 | DINP | 79 |
| 2 (according to the invention) | 3-methylbutyl/isononyl | 79 |
| 3 (according to the invention) | 3-methylbutyl/isononyl | 81 |
| 4 (comparison) | butyl/2-ethylhexyl | 76 |
| 5 (comparison) | butyl/isononyl | 77 |
| 6 (comparison) | butyl/isodecyl | 79 |

The plasticizing effect of the citric ester mixture according to the invention (plastisol 2) is the same as that of DINP.

It was thus possible to show that the citric ester mixtures according to the invention can replace the standard plasticizer DINP in particular in terms of the properties most important for plastisol processing, without altering the quantitative proportions of PVC and plasticizer.

Example 6

Determination of Volatility of Plasticizers by Thermogravimetric Analysis (TGA)

In order to define the volatility of the products, the losses in weight of the citric esters produced according to Example 1 were compared at relatively high temperatures by the dynamic TGA method. To this end, about 40 mg of a specimen were heated under nitrogen in DuPont Instruments TGA 951 equipment in the temperature range from 20 to 300° C. with a dynamic temperature rise of 10 K/min, and the respective loss in weight was determined in %.

FIG. 1 shows a comparison of the respective test curves.

The two citrates according to the invention exhibit smaller losses in weight in particular at the relatively high temperatures. This is surprising because the average chain length, and therefore also the average molar mass, is identical.

Example 7

Investigation for SVOC Components

An SVOC is a substance which elutes between the retention times of $C_{16}$ and $C_{22}$ n-paraffin on a non-polar GC column.

For simplicity, the only component investigated in all cases was the respective lowest-boiling component of the particular citrate ester mixture, i.e. tri-3-methylbutyl citrate in Cases 1 and 2 (according to Table 1) and tri-n-butyl citrate from Comparative Examples 3 to 5 (according to Table 1).

This investigation used gas chromatography on a non-polar column. The signal of the tributyl citrate here appeared immediately prior to the $C_{22}$ paraffin signal, and the signal for the tri-3-methylbutyl citrate appeared markedly later.

Tributyl citrate is therefore an SVOC, and items which comprise this plasticizer may sometimes exceed the maximum values. Tri-3-methylbutyl citrate is not an SVOC according to this definition, and there are therefore no restrictions here on the interior use of items manufactured therefrom.

In summary, it can be said that the citrate ester mixtures according to the invention could substantially replace DINP, which has hitherto been the standard plasticizer, without modification of formulations, and that they are unlike the comparative substances in comprising no components defined as SVOC. Furthermore, the plastisols based on the citrate plasticizers according to the invention exhibit markedly less viscosity rise over time, and processors therefore need to make fewer adjustments.

The invention claimed is:

1. A mixture of citric esters of the formula I,

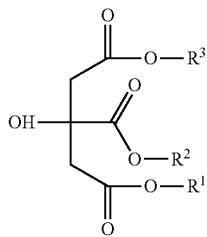

in which each of $R^1$, $R^2$ and $R^3$ is an aliphatic $C_5$ or $C_9$ moiety,
wherein
the average chain length of the aliphatic moieties in the mixture is in the range of from greater than 5 to 7, and the average degree of branching of the aliphatic $C_9$ moieties is in the range of from 0.9 to 2.2.

2. The mixture of citric esters according to claim 1, further comprising a mixture
of trinonyl and tripentyl citrates.

3. The mixture of citric esters according to claim 1, wherein the average chain length of the aliphatic moieties is in the range of from 5.5 to 6.8.

4. The mixture of citric esters according to claim 1, wherein
the $C_5$ moieties comprise at least 90% of n-pentyl and 3-methylbutyl moieties, based on the entirety of the $C_5$ moieties.

5. The mixture of citric esters according to claim 1, wherein
the $C_5$ moieties comprise at least 70% of 3-methylbutyl moieties, based on the entirety of the $C_5$ moieties.

6. The mixture of citric esters according to claim 1, wherein
the average degree of branching of the $C_9$ moieties is from 1.0 to 2.0.

7. A plasticizer composition comprising the mixture of citric esters according to claim 1.

8. The plasticizer composition according to claim 7, further comprising
at least one plasticizer selected from the group consisting of an alkyl ester of an aromatic polycarboxylic acid, an alkyl ester of a cyclohexanepolycarboxylic acid, an alkyl ester of benzoic acid, an alkyl ester of adipic acid, a dibenzoic ester of a diethylene glycol, a dibenzoic ester of a dipropylene glycol, a dibenzoic ester of a triethylene glycol, and a dibenzoic ester of a tripropylene glycol,
wherein the plasticizer composition contains from 15 to 90% by weight of the mixture of citric esters, the remainder to 100% by weight being the portions by weight of all the plasticizers.

9. A plastics composition, comprising the plasticizer composition according to claim 8.

10. A plastics composition according to claim 9, comprising
polyvinyl chloride (PVC).

11. A plastics composition according to claim 9, comprising
polyalkyl methacrylate (PAMA).

12. A plastics composition according to claim 9, comprising
polyvinyl acetate (PVAc).

13. A plastics composition according to claim 9, comprising
polyvinyl butyral (PVB).

14. A plastics composition according to claim 9, comprising
polylactic acid (PLA).

15. A plastics composition according to claim 9, comprising
polyhydroxybutyric acid (PHB).

* * * * *